US005466586A

United States Patent [19]

Davey et al.

[11] Patent Number: 5,466,586

[45] Date of Patent: Nov. 14, 1995

[54] METHOD FOR THE SYNTHESIS OF RIBONUCLEIC ACID (RNA)

[75] Inventors: Cheryl Davey, Toronto; Lawrence T. Malek, Brampton, both of Canada; Peter F. Lens, Amsterdam; Frits Wielaard, Den Bosch, both of Netherlands

[73] Assignee: Akzo Nobel N.V., Arnhem, Netherlands

[21] Appl. No.: 192,756

[22] Filed: Feb. 7, 1994

Related U.S. Application Data

[63] Continuation of Ser. No. 67,156, May 24, 1993, abandoned, which is a continuation of Ser. No. 941,846, Sep. 8, 1992, abandoned, which is a continuation of Ser. No. 521,292, May 9, 1990, abandoned.

[30] Foreign Application Priority Data

May 10, 1989 [NL] Netherlands .................... 8901172

[51] Int. Cl.$^6$ .................... C07H 21/00; C12N 15/10; C12P 19/34; C12Q 1/68
[52] U.S. Cl. .................... 435/91.21; 435/6; 435/91.1; 435/91.2; 435/172.3; 536/23.1; 536/24.1; 935/17; 935/19; 935/20; 935/78
[58] Field of Search .................... 435/91, 172.1, 435/172.3, 6, 91.2, 91.21, 91.1; 536/24.1, 23.1; 935/17, 19, 20, 78

[56] References Cited

U.S. PATENT DOCUMENTS

| | | | |
|---|---|---|---|
| 4,683,202 | 7/1987 | Mullis | 435/172.3 |
| 4,766,072 | 8/1988 | Jendrisak et al. | 435/91 |
| 5,409,818 | 4/1995 | Davey et al. | 435/91.21 |

FOREIGN PATENT DOCUMENTS

WO8810315  12/1988  WIPO.

OTHER PUBLICATIONS

Milligan et al., 1987, Nucleic Acids Research 15:8783–8798.
E. S. Stoflet et al., "Genomic Amplification with transcript sequencing", Science, vol. 239, Jan. 9, 1988, pp. 491–494, USA.
R. Higuichi et al., "A general method of in vitro preparation and specific mutagenesis of DNA fragments: study of protein and DNA interactions", Nucleic Acids Research, vol. 16, No. 15, Aug. 11, 1988, pp. 7351–7367, Great Britain.
Weier et al. (1988), Nucleic Acid Res., vol. 16, p. 11836.
Melton et al. (1987), Methods in Enzymology, pp. 288–296.

Primary Examiner—James Martinell
Assistant Examiner—Brian R. Stanton
Attorney, Agent, or Firm—Mary E. Gormley

[57] ABSTRACT

The invention relates to a method for the synthesis of ribonucleic acid (RNA) starting from deoxyribonucleic acid (DNA). In the method of the invention, a double stranded DNA molecule is cleaved with a restriction endonuclease so as to generate a free 3'-end. The resultant DNA molecule is then denatured and hybridized with a primer that anneals to the 3'-end of the denatured DNA. The primer used in the hybridization contains a T7 promoter sequence at its 5'-end. Following the hybridization step, the 3'-ends of the resultant hybrid DNA molecule are extended with DNA polymerase to generate a template suitable for T7 RNA polymerase mediated RNA synthesis.

3 Claims, No Drawings

METHOD FOR THE SYNTHESIS OF RIBONUCLEIC ACID (RNA)

This is a continuation of U.S. Ser. No. 08/067,156 filed May 24, 1993, now abandoned, which is a file wrapper continuation of U.S. Ser. No. 07/941,846, now abandoned, filed Sep. 8, 1992, which is a file wrapper continuation of U.S. Ser. No. 07/521,292, filed May 9, 1990, now abandoned.

The invention relates to a method for synthesizing RNA starting from deoxyribonucleic acid (DNA) containing specific nucleic acid sequences (target sequences).

A great deal of work in molecular biology relates to the isolation and/or detection of specific fragments of a nucleic acid sequence. A fundamental problem is to determine the quantity and/or presence of a specific fragment of a nucleic acid sequence after the isolation of a nucleic acid. This problem is not simple to solve because biological material, such as cell cultures and/or tissue cultures, and also body fluids, such as urine and blood, often contain a complex of nucleic acids of which only an extremely small fraction contains the sequence of interest. In U.S. Pat. No. 4,683,202 Cetus describes a method for replicating a target sequence in a so-called PCR (polymerase chain reaction) technique in order to solve this problem. By means of this technique, in which use is made of at least two primers which recognise fragments in the target sequence, the target sequence is replicated exponentially in a number of cycles. By using this technique a target sequence is replicated by a factor of approximately $10^5$ in 20 cycles over a period of 3 hours. It is then possible to detect the target sequence.

Very recently SISKA Diagnostics published a method in WO 88/10315 for generating RNA starting from a double-strand DNA fragment.

In order to arrive at this double-strand DNA fragment starting from a test fluid in which DNA is present, the said SISKA patent application one uses two primers, as is also described in the previously mentioned Cetus patent. According to the SISKA invention, one of the primers is provided with a promoter sequence, for example of a bacteriophage T7 promoter. RNA can then be transcribed using T7-RNA polymerase. This technique has the disadvantage, as is also the case with the technique described by Cetus, that two primers always have to be used in order to replicate the target sequence.

The present invention relates to a novel method for synthesizing RNA starting from deoxyribonucleic acid (DNA) in which a target sequence is present, by treating this DNA with one or more restriction enzymes, after which the DNA fragment thus obtained is rendered single-strand by a separation step, after which one nucleic acid primer containing a promoter sequence which is coupled to a nucleotide sequence which corresponds to part of the target sequence is hybridized under suitable conditions on the corresponding single-strand DNA, after which the two nucleic acid sequences obtained in hybrid form are extended from the free 3'-end by a DNA polymerase to give a double-strand DNA, which is then used by RNA polymerase as a matrix for synthesizing RNA.

The great advantage of this novel method is that, by using one or more restriction enzymes, only one nucleic acid primer, provided with a promoter sequence, is needed to be able to arrive at a double-strand DNA, from which RNA can subsequently be transcribed by RNA polymerase. Moreover, according to the invention, a separation step is required only once in order to be able to arrive at the abovementioned double-strand DNA.

This novel method provides many single-strand RNA fragments which correspond to the target sequence. This excess of RNA fragments, in relation to the target sequence started from, can be detected rapidly and simply with the aid of specific methods. One of these methods is that the synthesized RNA is detected by means of gel electrophoresis under denaturing conditions followed by blotting, after which hybridization with a labelled specific oligonucleotide sequence (probe) takes place. Suitable labelling substances are radioactive substances to be used for this purpose, such as $^3H$, $^{32}P$ or $^{35}S$. Those substances which can be converted under the influence of an enzymatic reaction, after which a detection is possible, are likewise suitable labelling substances. For example, an avidin/biotin complex is very suitable for this purpose.

The invention also relates to a test kit for synthesizing a RNA fragment starting from single-strand or double-strand DNA, the test kit comprising one or more restriction enzymes as well as one nucleic acid primer, provided with a promoter sequence, DNA polymerase and RNA polymerase.

The invention is illustrated in more detail with the aid of a detailed description of the method for synthesis of a RNA fragment starting from DNA in which a target sequence is present.

"Starting from deoxyribonucleic acid (DNA) in which a target sequence is present" means that the method according to the invention can begin with either double-strand DNA or single-strand DNA.

The term "target sequence" signifies a sequence present in the total DNA, frequently termed the genome, which it is desired to detect. A target sequence of this type can code for a specific protein which, for example, is a constituent of a coating protein of a virus.

If the method is started from double-strand DNA, a target sequence can be removed from the genome by making use of one or more restriction enzymes. For this purpose restriction enzymes can be used which generate either defined overlapping ends ("sticky ends") or knotted-off defined ends ("blunt ends"). Preferably, restriction enzymes are used which recognize a sequence of 4 or 6 nucleotides on the DNA.

If the method is started from single-strand DNA excellent use can be made of an endonuclease which belongs to the class IIs restriction enzymes, such as, for example, the Fok I enzyme. Details of the action and the characteristics of this enzyme are described in an article by Podhajska and Szybalski (Gene, 40(1985), 175–182). With the aid of enzymes of this type it is possible to remove a target sequence from single-strand DNA.

Subsequently the two strands of a target sequence consisting of a double-strand DNA must be separated. A separation of this type can take place in the conventional manner by raising the temperature or by an enzymatic reaction, for example the use of a helicase or topo-isomerase, or by a chemical reaction, such as treatment with lye.

Subsequently "a nucleic acid primer containing a promoter sequence which is coupled to a nucleotide sequence which corresponds to part of the target sequence" is hybridized under suitable conditions on the single-strand DNA molecules thus obtained which contain the target sequence with free 3'-ends generated by restriction enzymes.

The term nucleic acid primer signifies a nucleic acid sequence (made via an organic chemical synthesis or obtained via a recombinant DNA technique) which possesses sufficient homology with the target sequence so that, under suitable conditions, the nucleic acid primer can hybridize on the target sequence. Frequently a primer is at least 10 nucleotides long and preferably approximately 35 nucleotides long.

"Promoter sequence" means a nucleic acid sequence (made via an organic chemical synthesis or obtained via a recombinant DNA technique) which is recognized specifically by a RNA polymerase. A RNA polymerase of this type binds to a recognition sequence and starts the transcription process by which a RNA fragment is made. In principle, any promoter sequence can be used for which a RNA polymerase is available. Suitable promoters are those which are recognized by specific bacteriophage polymerases, such as bacteriophage T3, T7 or SP6. T7 and SP6 RNA polymerase are preferred.

"The promoter sequence is coupled to a nucleotide sequence which corresponds to part of the target sequence" means that said promoter sequence is coupled directly or indirectly, via one or more nucleotides, in a manner known per se to the nucleotide sequence which is recognized by at least part of the target sequence. Said recognition takes place if sufficient homology exists under suitable conditions between the nucleotide sequence and the target sequence.

After the hybridization of the nucleic acid primer, carried out under suitable conditions, the two nucleic acid sequences obtained in hybrid form are extended from the free 3'-end by a DNA polymerase to give a double-strand DNA fragment.

Suitable DNA polymerases for this purpose are *E.coli*, DNA polymerase I, Klenow fragment of *E.coli* DNA polymerase I, T4 DNA polymerase, AMV reverse transcriptase, MMLV reverse transcriptase and the like.

The RNA which is subsequently synthesized from the generated double-strand DNA by a suitable RNA polymerase is synthesized more or less continuously depending on the quantity of RNA polymerase present.

The synthesized RNA can then be detected by one of the previously described methods according to the invention. If it is desired to detect several RNA molecules, the RNA already synthesized can be multiplied by known amplification techniques.

An example of an amplification technique of this type is described in a patent application (WO 88/10315) by SISKA Diagnostics.

The invention is illustrated in more detail with the aid of a non-limiting example which follows.

EXAMPLE I

DNA is isolated from $10^8$ white blood cells from a patient with a probable CMV (cytomegalovirus) infection using a standard procedure (Maniatis, CSH): proteinase K digestion, phenol/chloroform extraction followed by alcohol precipitation.

After dissolving DNA in EcoRV digestion buffer (10 mM Tris pH 7.5, 7 mM $MgCl_2$, 7 mM 2-mercaptoethanol, 100 mM NaCl, 100 µg/ml bovine serum albumin) to a concentration of 1 µg/µl, 3 units EcoRV restriction enzyme are added per µg DNA and this is followed by 2 hours digestion at 37° C. EcoRV restriction enzyme recognizes a sequence in the CMV-DNA, for example nucleotide numbers 2069 to 2074 (according to Akrigg in Virus Research, 2, 1985, 107–121) and yields a blunt end fragment.

Subsequently the DNA-containing sample is heated at 95° C. for 10 minutes (boiling water bath or in a heat block) in order to denature the DNA. The sample is cooled rapidly on dry ice. 2 µg of a primer consisting of 55 nucleotides (see Formula I) are added and primer annealing takes place at 65° C. for 1 minute and then at 42° C. for 1 minute. 20 units Avian Myeloblastosis Virus Reverse Transcriptase are added in the presence of 200 µM dATP, 200 µM dTTP, 200 µM dGTP, 200 µM dCTP, 1 mM ATP, 1 mM GTP, 1 mM CTP and 1 mM UTP and the mixture is incubated at 42° C. for 15 minutes. RNasin® from Promega Biotec is added as ribonuclease inhibitor in a concentration of 1 unit per ml (1 unit is 50% of the amount of inhibitor which is necessary to inhibit the activity of 5 µg RNase-A). T7 RNA polymerase is added and the mixture is incubated at 37° C. for 25 minutes.

For detection of the transcripts, the sample is denatured in 7.4% (vol/vol) formaldehyde/10×SSC at 55° C. for 20 minutes. After cooling on ice, the samples are immobilized on a nitrocellulose membrane with the aid of a slot-blot apparatus (Bio Rad).

The filters are pre-hybridized at 55° C. for 10 minutes in 0.5% bovine serum albumin/0.5% polyvinylpyrrolidone/5× SSPE/1% SDS and then hybridized in the same buffer with a $^{32}$P-labelled oligonucleotide probe 5'-GAT GGC CCC GTA CAT GGT CAT CAT ACA AGC-3' ($2–5\times10^6$ cpm/ml), this being a sequence located between nucleotide numbers 2155 and 2126 in the correct polarity.

The filters are hybridized for 1 hour at 55° C. and then washed for 3×5 minutes at room temperature with 1×SSPE/ 1% SDS and for 2 minutes at 55° C. Autoradiography takes place over a period of 16 hours at −70° C. using a so-called "intensifying screen".

The autoradiogram confirms that CMV-RNA transcripts can be synthesized from a DNA matrix with the aid of the method according to the invention.

Formula I

Primer consisting of 55 nucleotides containing a T7 RNA polymerase binding site and a transcription initiation site as well as a sequence (30-mer) which corresponds to part of the CMV target sequence to be detected.

5'-AAT TTA ATA CGA CTC ACT ATA GGGA ATC CTC ACT ACA TGT GTG GAA ACA ATG TGT-3'

We claim:

1. A method for the synthesis of ribonucleic acid (RNA) from single stranded or double stranded deoxyribonucleic acid (DNA) in which a target sequence is present, comprising:

treating the DNA with one or more restriction enzymes to thereby generate a free 3' end of the target sequence;

rendering the DNA thus obtained single stranded;

hybridizing a single nucleic acid primer comprising a T7 promoter coupled to the 5' of a nucleic acid sequence that is complementary to the 3' end, including the ultimate nucleotide, of one of the strands of the target sequence;

extending the 3' ends of the resulting hybrid DNA molecules with DNA polymerase to produce a functional double stranded DNA template, in the absence of an additional primer, for synthesizing RNA; and transcribing said template by incubating it with an RNA polymerase that recognizes the T7 promoter sequence to obtain RNA.

2. The method according to claim 1, further comprising detecting the synthesized RNA by means of gel electrophoresis under denaturing conditions, followed by immobilizing the RNA onto a solid phase and detecting the immobilized RNA by hybridizing with a labeled oligonucleotide sequence that is complementary to the RNA.

3. A method for the synthesis of a double stranded DNA template that has a promoter site, comprising:

treating DNA with one or more restriction enzymes to thereby generate a free 3' end of the target sequence;

rendering restriction fragments thus obtained single stranded;

hybridizing the resulting single stranded DNA with a single nucleic acid primer comprising a T7 promoter sequence coupled to the a 5' of sequence complementary to the 3' end, including the ultimate nucleotide, of a single strand of the one of the restriction fragments; and extending the 3' ends of the resulting hybrid DNA with a DNA polymerase to produce a functional double stranded DNA template, in the absence of an additional primer, for synthesizing RNA.

* * * * *

UNITED STATES PATENT AND TRADEMARK OFFICE
CERTIFICATE OF CORRECTION

PATENT NO. : 5,466,586
DATED : November 14, 1995
INVENTOR(S) : Davey et al.

It is certified that error appears in the above-indentified patent and that said Letters Patent is hereby corrected as shown below:

Column 5, claim 3, line 10, after "the", delete "a" and

After "of" insert --a --.

Signed and Sealed this

Sixteenth Day of April, 1996

Attest:

BRUCE LEHMAN

Attesting Officer

Commissioner of Patents and Trademarks